(12) United States Patent
Shaw et al.

(10) Patent No.: US 11,430,315 B2
(45) Date of Patent: Aug. 30, 2022

(54) PERSONAL PROXIMITY ALERT DEVICE AND ASSOCIATED BEHAVIOR MODIFICATION SYSTEM

(71) Applicants: ConserVention, Inc., Frisco, TX (US); Thomas J. Shaw, Frisco, TX (US)

(72) Inventors: Thomas J. Shaw, Frisco, TX (US); Steven E. Shaw, Prosper, TX (US); Mark Small, Heavener, OK (US); Steve Wisner, Frisco, TX (US)

(73) Assignee: ConserVention, Inc., Little Elm, TX (US)

( * ) Notice: Subject to any disclaimer, the term of this patent is extended or adjusted under 35 U.S.C. 154(b) by 0 days.

(21) Appl. No.: 17/174,806

(22) Filed: Feb. 12, 2021

(65) Prior Publication Data

US 2021/0248890 A1 Aug. 12, 2021

Related U.S. Application Data

(60) Provisional application No. 63/075,716, filed on Sep. 8, 2020, provisional application No. 63/005,002, filed on Apr. 3, 2020, provisional application No. 62/975,561, filed on Feb. 12, 2020.

(51) Int. Cl.
| | | |
|---|---|---|
| *G08B 21/02* | (2006.01) | |
| *G08B 21/18* | (2006.01) | |
| *G08B 21/24* | (2006.01) | |
| *G08B 21/22* | (2006.01) | |

(52) U.S. Cl.
CPC .......... *G08B 21/02* (2013.01); *G08B 21/182* (2013.01); *G08B 21/22* (2013.01); *G08B 21/245* (2013.01)

(58) Field of Classification Search
CPC .... G08B 21/02; G08B 21/182; G08B 21/245; G08B 21/22; A61B 5/01; A61B 5/015
USPC ........................................................ 340/686.6
See application file for complete search history.

(56) References Cited

U.S. PATENT DOCUMENTS

| | | | |
|---|---|---|---|
| 7,476,102 B2 | 1/2009 | Maples | |
| 7,578,615 B2 * | 8/2009 | Ahmad | ................... G01W 1/17 702/131 |
| 9,301,689 B2 * | 4/2016 | Vanderpohl | .......... A61B 5/0077 |
| 10,842,431 B2 * | 11/2020 | Arai | ........................ A61B 5/026 |
| 10,847,017 B1 * | 11/2020 | Haseltine | ............... G08B 21/22 |
| 10,973,439 B2 * | 4/2021 | Douglas | ................ A61B 5/1112 |
| 2004/0160326 A1 * | 8/2004 | Zarouri | .................. G08B 21/18 340/573.1 |
| 2011/0254682 A1 * | 10/2011 | Sigrist Christensen | ..................... G08B 21/245 340/539.12 |
| 2012/0276525 A1 | 11/2012 | Kovarik et al. | |
| 2015/0381609 A1 | 12/2015 | Dadu et al. | |
| 2016/0140830 A1 * | 5/2016 | Hathorn | ................. G08B 21/18 340/686.6 |

* cited by examiner

*Primary Examiner* — John A Tweel, Jr.
(74) *Attorney, Agent, or Firm* — Monty L Ross PLLC; Monty L Ross

(57) ABSTRACT

A personal proximity alert device and associated behavior modification system configured to monitor and/or detect a hand of a user or another person or object penetrating a personal protection zone around the facial area of the user and to alert users to such detected risks and/or to the presence of others approaching within a predetermined minimum socially safe distance to reduce the likelihood of accidentally transmitting viruses or other pathogens.

20 Claims, 10 Drawing Sheets

PERSONAL PROXIMITY ALERT DEVICE AND ASSOCIATED BEHAVIOR MODIFICATION SYSTEM

FIELD OF THE INVENTION

This invention relates to a device and system useful for reducing the spread of contagious viruses, bacteria and other pathogens among persons who may otherwise be at risk of becoming infected, especially during the present corona virus (COVID-19) pandemic that has expanded world-wide during recent months. Although health organizations and governmental agencies have repeatedly communicated general warnings and specialized guidelines to the populace regarding the importance of disinfecting, hand washing, facial touching, social distancing and the wearing of masks to reduce the transmission of such pathogens by social, interpersonal or physical contact and aerosolization (such as by coughing, sneezing, speaking or even breathing within a crowded or confined space), new, improved and cost-efficient articles, devices and systems are still needed to assist families, health care workers and other first responders, educators, students, employees, business managers and operators of elderly care and prison facilities, for example, in identifying, recording, reporting and tracking symptomatic or asymptomatic carriers, maintaining appropriate social distancing with integrated risk-alert and warning systems, and behaviorally training or conditioning persons to avoid facial self-touching or physical contact with objects or surfaces likely to pose a risk of viral contamination.

DESCRIPTION OF RELATED ART

Recent events surrounding the onset and rapid spread of the corona virus have brought to mind similar prior events relating to contagions and epidemics such as Ebola, SARS, and Legionnaires disease, more common strains of influenza, and even the common cold. Such epidemics can have tremendous societal impact and create stress in many different aspects of life, including for example, healthcare resources, workplace environments, schools and other public facilities, as well as entire industries such as transportation, manufacturing, entertainment, food preparation and delivery, hospitality and the like.

Viruses, germs and pathogenic contaminants can be spread by direct physical contact between people, or between people and contaminated objects, or by airborne transmission as a result of contaminated dust particles or respiratory droplets that become aerosolized when an infected person sneezes or coughs. Communicable diseases are often spread by the successive physical touching of an object or another person. Door handles, seat belts, gasoline pumps, money and furniture are all examples of ordinary objects that are commonly touched or handled by numerous people in a single day and can contribute to the spread of contagions or disease. Tools, devices, substances and procedures used to limit the spread of contagious diseases have typically included: quarantine, physical segregation and isolation of infected or exposed individuals; protective masks, gloves and other clothing; antiseptic and disinfectant liquids, sprays and wipes; irradiation; precautionary body temperature monitoring and medical testing; and the like. Despite many efforts to control the spread of contagious diseases, significant problems remain—in part because of inter-personal contact and in part because of the vast number of different physical objects that are handled each day by the general populace while attempting to engage in their usual daily activities.

Another significant contributor to the spread of infectious diseases can be personal "self-touching" that occurs when an individual who may have handled or contacted previously contaminated objects, surfaces or other persons with hands or fingers subsequently touches a portion of her or his own face or head (collectively referred to below as "facial self-touching"). Such facial self-touching is often unintentional or habitual, or is done subconsciously or reflexively, such as a nervous "tic," or in response to a stimulus such as an itch or other sensation, often without realization by the person doing the touching. A device and system are therefore needed that can sense or detect a person's hand or fingers moving toward the same person's head or face; that can provide an audible, visible or tactile alert that will cause the person to change or redirect her or his behavior to avoid such inadvertent or unintended facial self-touching, and optionally count and save or record the number of proximal hand approaches and/or self-touches that occur within a measured interval. Such a device and system are desirably susceptible to high-speed, low-cost manufacturing, light in weight, durable and dependable, with a service life sufficient to withstand repeated cycles of operation over a reasonable use period without recharging, service, maintenance or replacement of component parts. Such a device and system are not believed to be presently available but are disclosed below.

Because appropriate social distancing (i.e., maintaining physical separation of at least three feet, and preferably six feet or more between persons) has also been recognized as a critical factor in controlling the interpersonal transmission of pathogenic contaminants, a need exists for improved articles, devices and systems capable of monitoring, sensing, reporting, warning, tracking, recording, tracing and communicating the movements of people who are going about their daily activities. Devices and systems useful for achieving those purposes are disclosed here.

SUMMARY OF THE INVENTION

In one embodiment of the invention, a personal proximity alert device and behavior modification system are disclosed that are configured to reduce occurrences of facial self-touching and thereby also reduce the likelihood of spreading infectious pathogens or contaminants present on the hands of a user to one or more parts of the user's facial area, and especially to the areas around the mouth, eyes or nose of the user, which are likely to facilitate the spread of such infectious pathogens or contaminants to the digestive, circulatory, neural or pulmonary systems of the user.

In another embodiment of the invention, a personal proximity alert device and behavior modification system are disclosed that can generate an audible, visible or tactile alert whenever a user's face or hands are moved to a position proximal to the face for the purpose of modifying the user's behavior to reduce occurrences of facial self-touching.

In another embodiment of the invention, a personal proximity alert device and behavior modification system are disclosed that can count and record, save or transmit the number of times at least a part of a hand of the user penetrates a "personal protection zone" around the user's facial area within a requisite counting period.

In another embodiment of the invention, a personal proximity alert device and behavior modification system are disclosed that can count and record, save or transmit the number of times at least part of the hand of a user contacts the facial area of the user within a requisite counting period.

In another embodiment, a personal proximity alert device and behavior modification system are disclosed that has an infrared (IR) sensor and an ancillary temperature recording device that can monitor or determine and record, save or transmit the facial temperature of the user at requisite times for the purpose of ascertaining whether the user may have become infected by an infectious pathogen.

In another embodiment, the personal proximity alert device of the invention system satisfactorily comprises at least one detection member (such as infrared (IR) sensors) for detecting temperatures or separation distances, and at least one alert notification member that communicate cooperatively to alert the user whenever a part of at least one hand of a user penetrates a "personal protection zone" disposed around the facial area of the user or when two or more users of such devices or systems are moving toward or into a proscribed area or have violated a minimum separation distance as determined, for example, by signal strength or by GPS positioning.

In another embodiment, the behavior modification system of the invention satisfactorily comprises a personal proximity alert device having the capability to communicate with other devices, networks or systems (i.e. fit bit, WAN, medical database, etc.) and such communication capability may be achieved via wired (i.e. USB, Ethernet, etc.) or wireless methods (i.e. Wi-Fi, Bluetooth, cellular, etc.) If desired, the subject device and system can also be configured to record, save or transmit user data regarding facial touches or near-touches for personal use, or for subsequent contact tracing or for use in generating new alerts. Such technology can also be used to time stamp occurrences, generate data logs, and prepare maps that are helpful in cataloging and distributing information useful in monitoring high-risk areas or for controlling participation in so-called "super-spreader" events In another embodiment, the invention comprises a personal proximity alert device that detects a finger, thumb or hand of a user moving toward the head or face of the user and alerts the user to pending physical contact before such contact occurs and, preferably, sufficiently in advance of such contact that the user is able to respond by controlling the movement to prevent the physical contact from occurring. In addition to usefulness for retraining users of the methods, devices and systems disclosed here, when such tools and practices are adopted and implemented over time by large groups of users, significant reductions in the spread of COVID or other pandemic viruses can be achieved.

In another embodiment, the subject invention can include a touch sensor that is worn on the hand(s), finger(s) or wrist of a user and is configured to generate an electronic pulse whenever a touch surface makes contact with a part of the facial area of the user. Alternatively, touch, temperature, or positional sensing and notification devices and systems can be incorporated into wearable garments, hats, shoes, jewelry and the like to assist in alerting, warning or protecting a user or bystander of potential risk, or in behaviorally conditioning a user to observe and maintain desirable social distancing and other safe behaviors.

In another embodiment, the personal proximity alert device and behavior modification system of the invention satisfactorily comprises, in addition to a detection member and an alert notification member, one or more of the following ancillary devices: a preprogrammed or programmable controller; a power supply; a transmitter/receiver; a timer; a proximity zone penetration counter; a facial self-touch counter; and a data storage or recording device.

In another embodiment, a time interval between detection and alert notification can be preset using an electronic controller or timer, and can vary in accordance with factors such as the proximity of the hand to the face and the speed and direction of hand movement relative to the head or face. The interval is desirably sufficient to enable the user to react and respond by moving the user's hand(s) and/or head to avoid or reduce the likelihood of physical contact that would constitute facial self-touching.

The detection member and the alert notification member of the personal proximity device can be configured within a single element or can be separately configured into two or more elements disposed apart from each other. The physical configuration of the personal proximity alert device and behavior modification system of the invention can also vary according to the particular detection technology selected for use in the detection member and in the alert notification member of the device. For example and without limitation, the detection technology can be based upon and include commercially available components configured to implement magnetic, acoustic, infrared, radio frequency or optical (laser) detection. The detection member of the subject device can be directional or non-directional. If the subject device is used primarily at a time when the user is sitting, for example, a properly positioned and calibrated detection member will be effective to trigger an alert notification if the user's hands move into a defined personal protection zone toward the head or face from any direction. The subject system can also be utilized for detecting proximity to the face as opposed to proximity to a sensor.

Depending upon the particular components selected for use in the detector member and the alert notification member of the personal proximity alert device and behavior modification system of the invention, a suitable power supply such as rechargeable or non-rechargeable batteries can be provided as part of the subject system.

For some devices and systems of the invention, elements of the detection member or of the alert notification system may be worn attached to or embedded in one or more of the following: a cap, visor or headband; one or more wristbands, watch, bracelet or ring; in a pin or pen; in ear-pods or earplugs; in eyeglasses; in a necklace or choker; or hanging from a short lanyard worn around the neck. In one embodiment of the invention, for example, laterally spaced-apart detection members are disposed at each side of eyeglass frames and an audio alert notification generator and battery are disposed inside one of the earpieces. In one alternate embodiment of the invention, the detection member has a detection member and a visual alert notification member mounted forwardly of the user's eyes in the bill of a visor worn on the user's head. In still another embodiment of the invention, the detection member comprises two laterally opposed detection elements disposed in pull-out slides situated on each side of a head support collar worn around the neck of the user, with a tactile alert notification member and rechargeable battery disposed in the base of the collar behind the user's head. In still another embodiment of the invention, one or more mirrors disposed beneath or forwardly of the bill of a cap can receive and redirect infrared radiation from the face of a user to an IR sensor and recorder or alert system adapted to notify a wearer if his or her own facial temperature exceeds a predetermined norm for a sufficient period of time.

The alert notification member of the invention can be satisfactorily configured to receive a communications signal or other input from the detection member of the subject personal proximity alert device and then quickly trigger an audible, visible or tactile alert to the user. An audible alert can, for example, be a beeper producing a readily identifiable audio signal sufficiently loud to get the immediate attention of the user. If the subject device and system are used regularly, the sounding of the audible alert should condition the user to initiate a reflexive response that will cause her or his hands to be drawn away from the user's face, thereby successfully interrupting the facial self-touching behavior. With an alert notification member that generates a visual signal, a solid or blinking LED bulb readily visible to the user can similarly condition the user to move her or his hands away from the face and refrain from self-touching for at least a short interval. With an alert notification member that generates a tactile alert in response to movement of the hands or fingers toward the head or face of the user, a small motor having an eccentrically mounted rotor or another similarly effective device will generate a tactile stimulus sufficient to produce the desired response.

In another embodiment of the invention, a small plastic box with a belt clip worn on the belt or waistband of a user satisfactorily comprises a selectively programmable processor operatively coupled to a rechargeable battery and an associated transmitter/receiver configured to communicate wirelessly with a pair of motion detection sensors configured as earplugs that also generate and play an audible alert when signaled by the processor in response to movement of the user's hands toward her or his face.

The personal proximity alert notification system of the invention can be configured to operate with or without interaction or input from the user, and any alert notification can be selectively disabled if desired. While primarily intended for the principal purpose of reminding and conditioning users to refrain from unintentional facial self-touching and thereby reduce the likelihood of spreading infectious diseases, viruses and other biologically hazardous contaminants, it will be appreciated upon reading this disclosure that the subject invention can also be used or reconfigured for use to achieve other beneficial purposes and results.

BRIEF DESCRIPTION OF THE DRAWINGS

The invention is further described and explained in relation to the following drawings wherein.

DESCRIPTION OF PREFERRED EMBODIMENT

Figure 1:
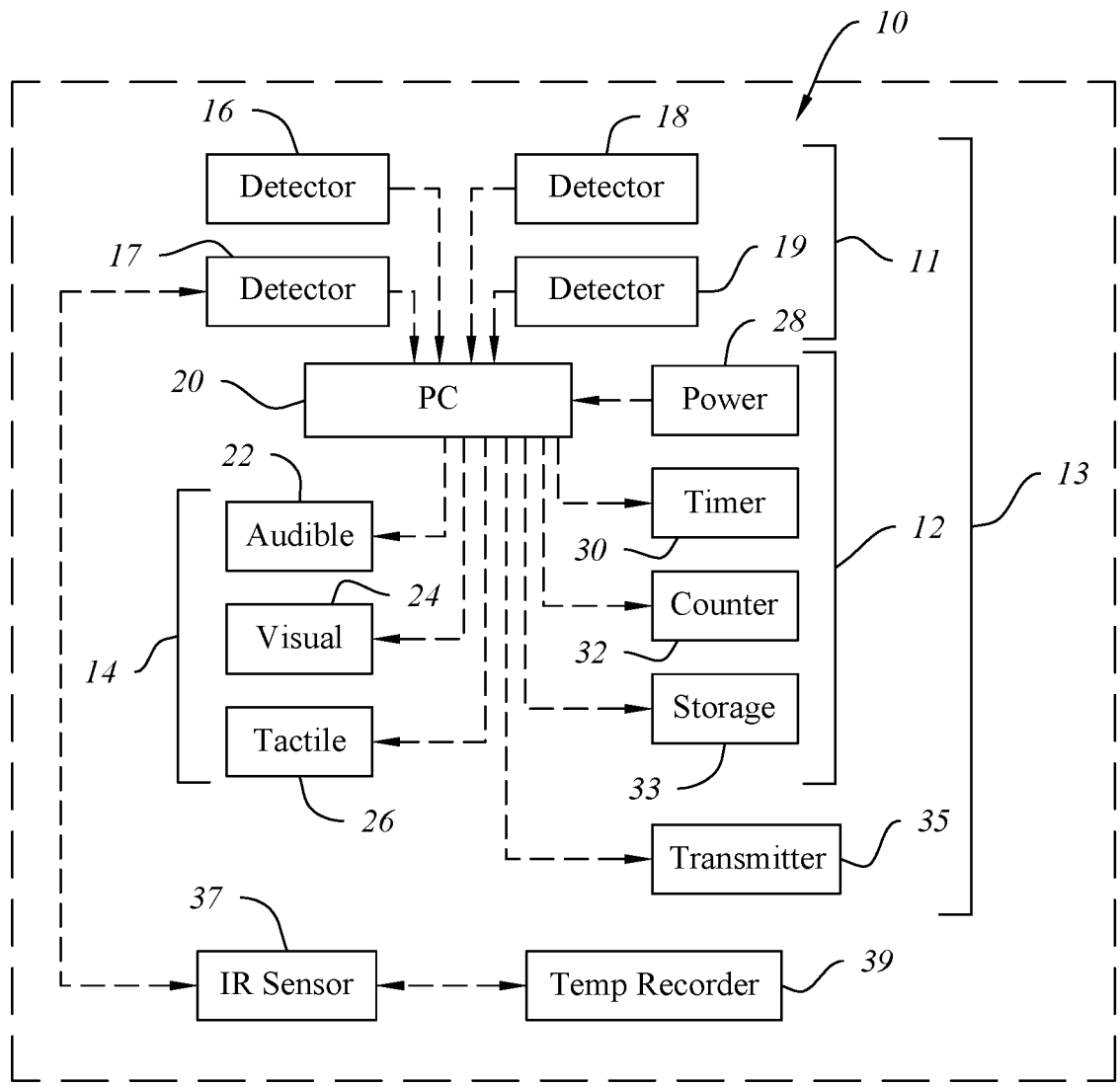
FIG. 1 is a simplified diagrammatic view of one embodiment of a personal proximity alert device and behavioral modification system of the invention.

Referring to the embodiment of FIG. 1, behavior modification system 10 of the invention satisfactorily comprises personal proximity alert device 13 further comprising a plurality 11 of detector members 16-19 and alert notification member 12. Alert notification member 12 satisfactorily comprises preprogrammed or programmable controller 20 that cooperatively communicates with detector members 16, 18 and with alert generators 14, power supply 28, timer 30, touch and near-touch counter 32 and data storage member 33. Alert generators 22, 24, 26 satisfactorily include one or more of audible alert generator 22, visual alert generator 24 and tactile generator alert 26. Other ancillary components of alert notification member 12 of behavior modification system 10 are also disclosed but not and can include a transmitter 35, IR sensor 37 and temperature recording device 39 depicted in FIG. 1.

Figure 2:
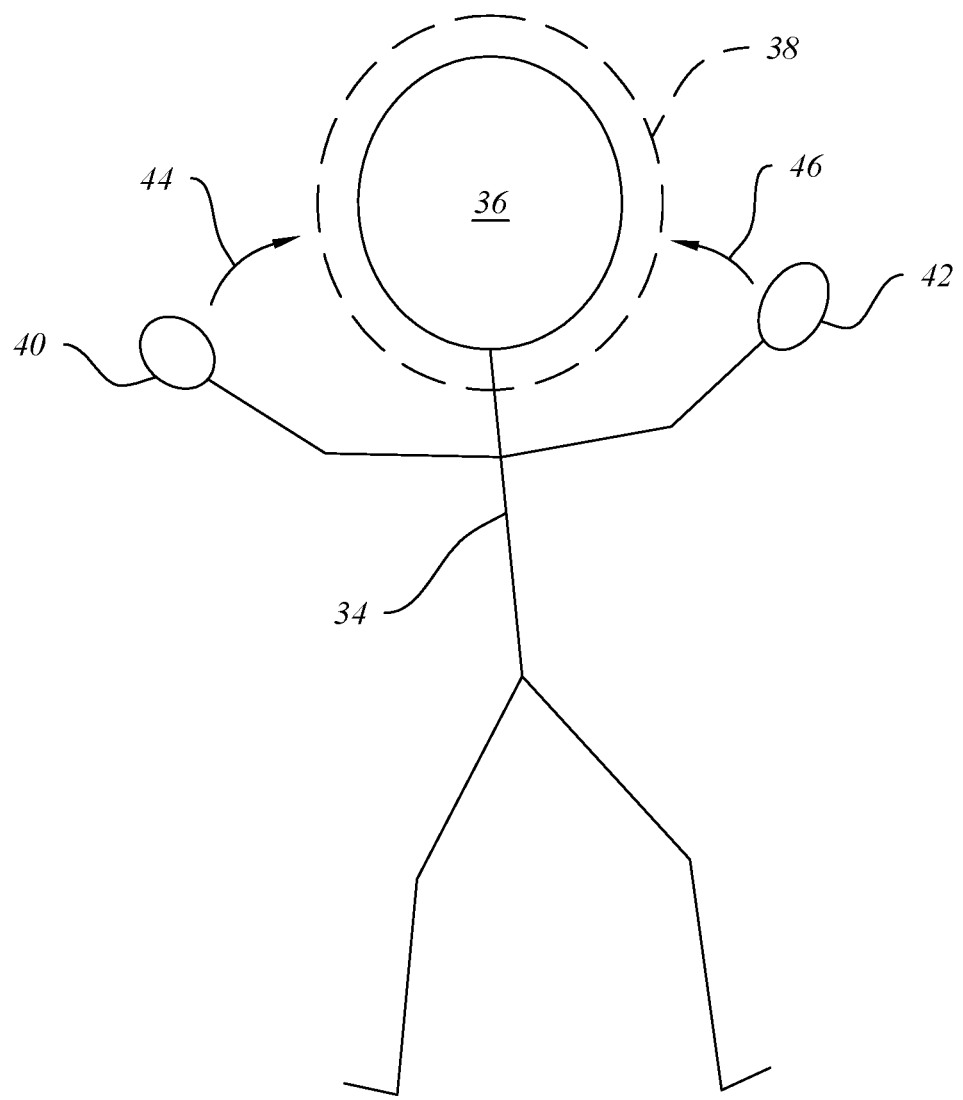
FIG. 2 is a simplified diagrammatic view of a personal protection zone disposed around the facial area of a user.

Referring to FIG. 2, user 34 embodies facial area 36, personal protection zone 38 disposed around facial area 36, and left and right hands 40, 42, respectively. Arrows 44, 46 diagrammatically depict how hands 40, 42, respectively of user 34 can be moved upwardly and inwardly to move into or penetrate personal protection zone 38, thereby causing personal proximity alert device 13 of behavior modification system 10 to alert user 34 to assist user 34 in modifying her or his behavior so as to avoid making physical contact between either of hands 40, 42 and facial area 36.

Although not depicted in the drawings, several examples of the manner in which detectors 16, 18 and personal proximity alert device 13 can be configured or worn for use by user 34 in association with behavior modification system 10 of the invention are disclosed in the preceding text and will become apparent upon reading the specification in connection with the drawings provided.

Figure 3:
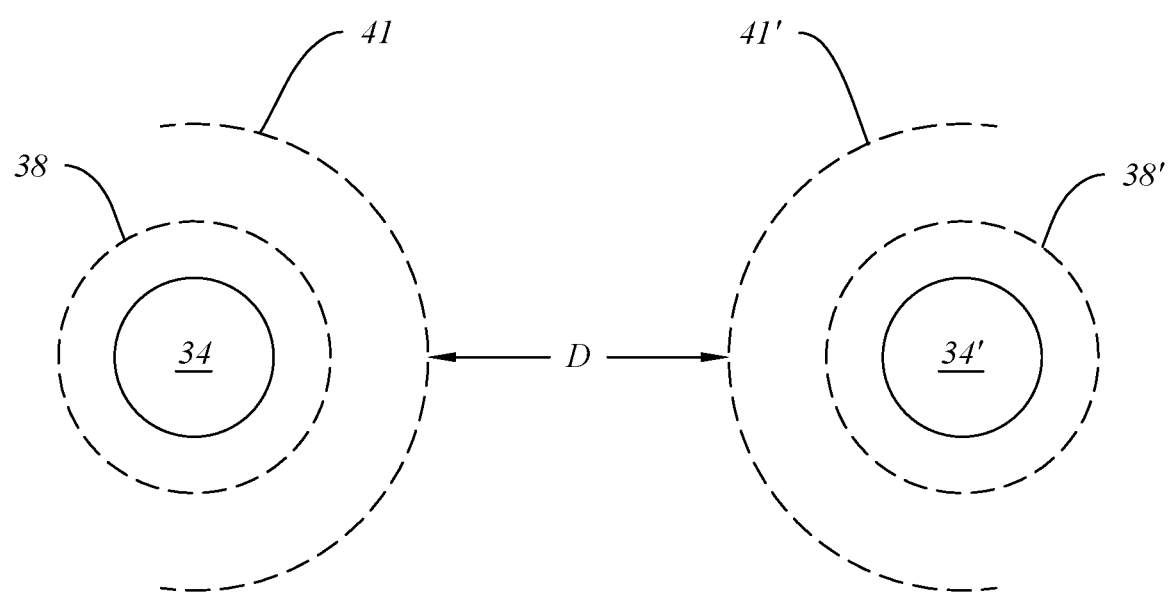
FIG. 3 is a simplified diagrammatic view illustrating an two individuals each surrounded by a personal protection zone and an alert notification zone, with the two respective alert notification zones being separated by a distance "D;"

Referring to FIG. 3 of the drawings, two users 34, 34' of an embodiment of system 10 of the invention each have a personal protection zone 38, 38' and an arc 41, 41' disposed at a predetermined minimum distance from the respective user 34, 34'. As shown, arcs 41, 41' are themselves separated by a distance "D" that users 34, 34' will desirably maintain as the minimum acceptable social distancing between themselves (preferably at least about 6 feet) through use of system 10 of the invention. As one user 34, 34' gets closer to the other, both users 34, 34' are desirably alerted to the approach of another person who could be a carrier of a transmittable pathogenic infection. In this case, a notification alert should desirably be provided to each user.

Figure 4:
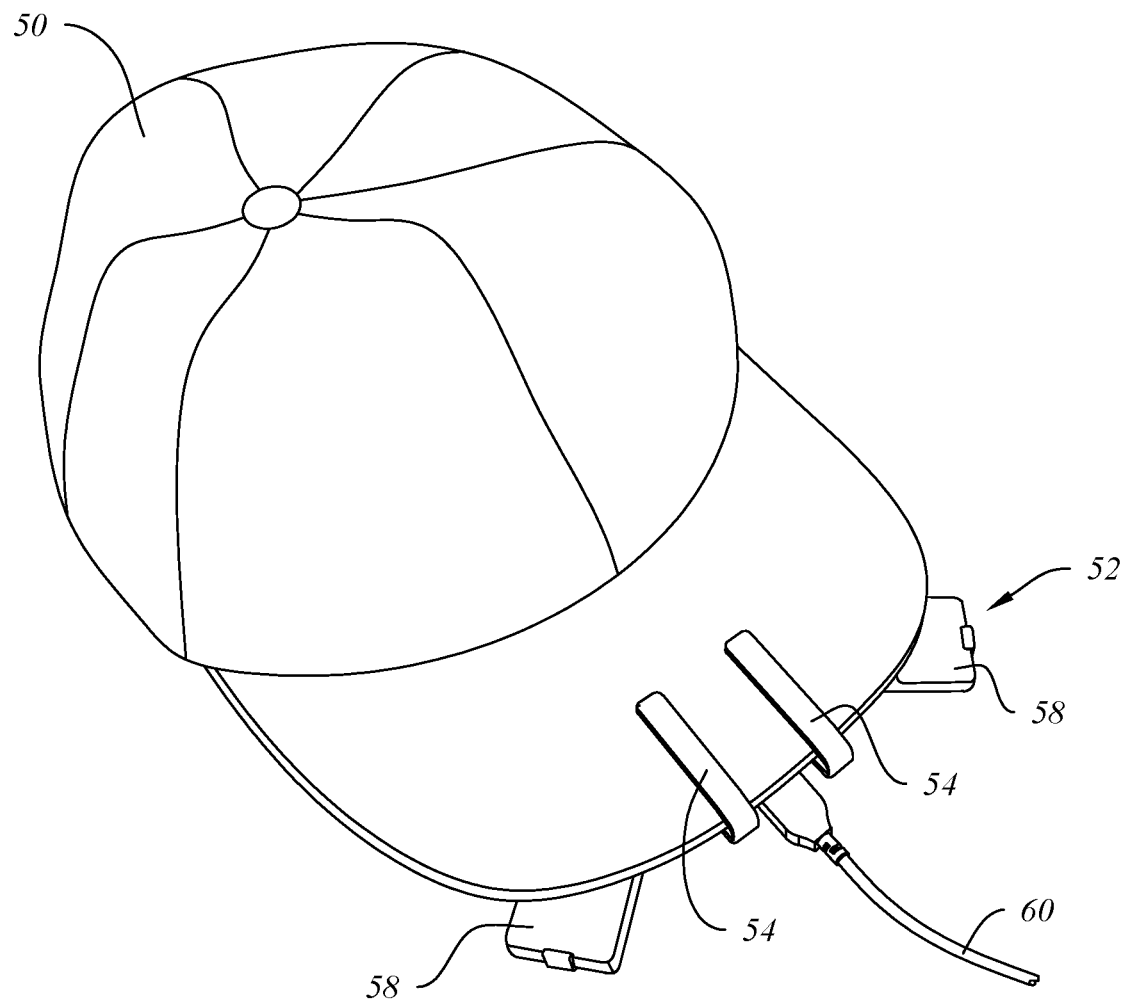
FIG. 4 is a top perspective view of a cap having releasably attached to one embodiment of a personal proximity alert device of the invention.
Figure 5:
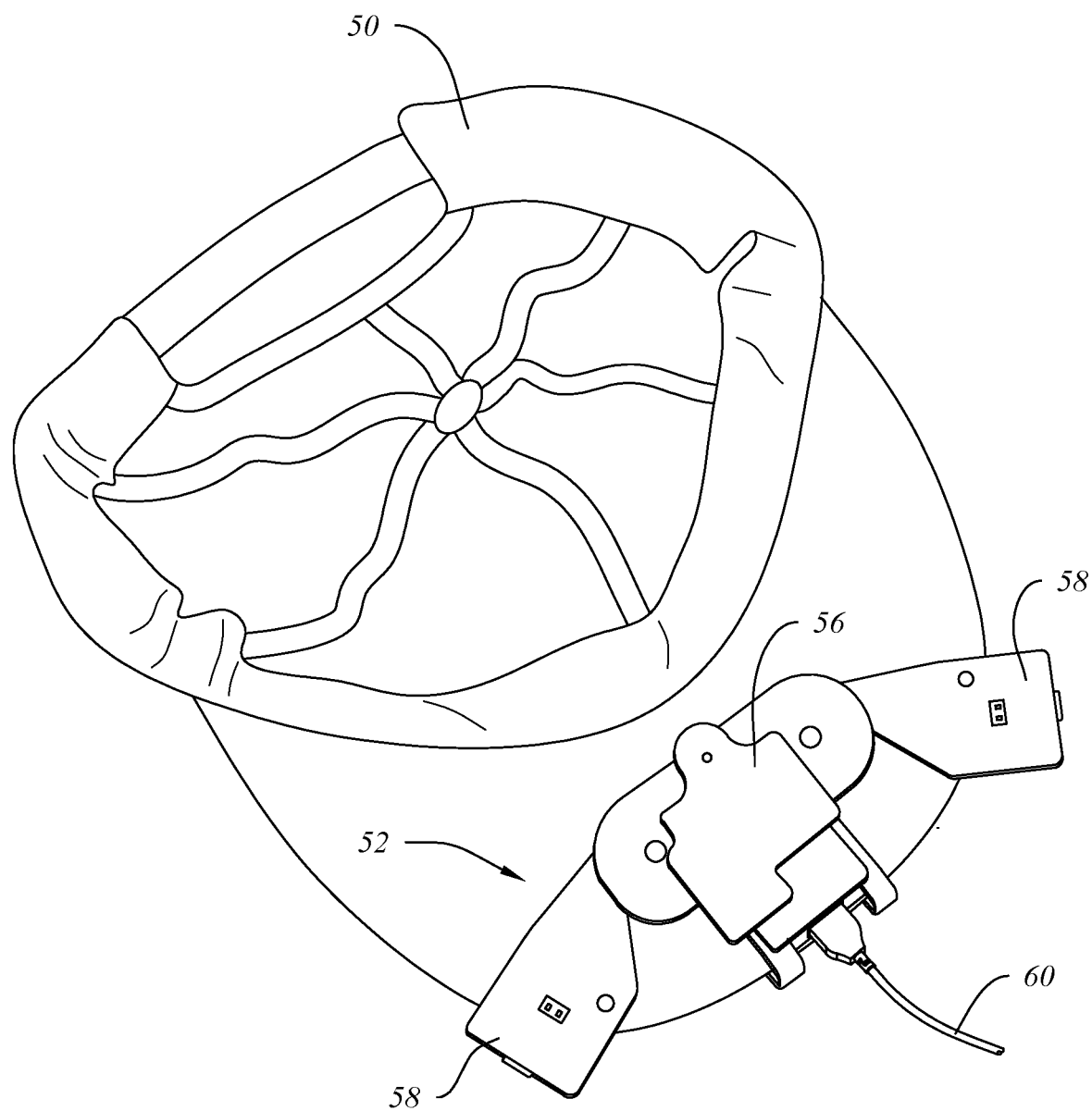
FIG. 5 is a bottom perspective view of the cap of FIG. 4 with one embodiment of a personal proximity alert device disposed under the bill of the cap.
Figure 6:
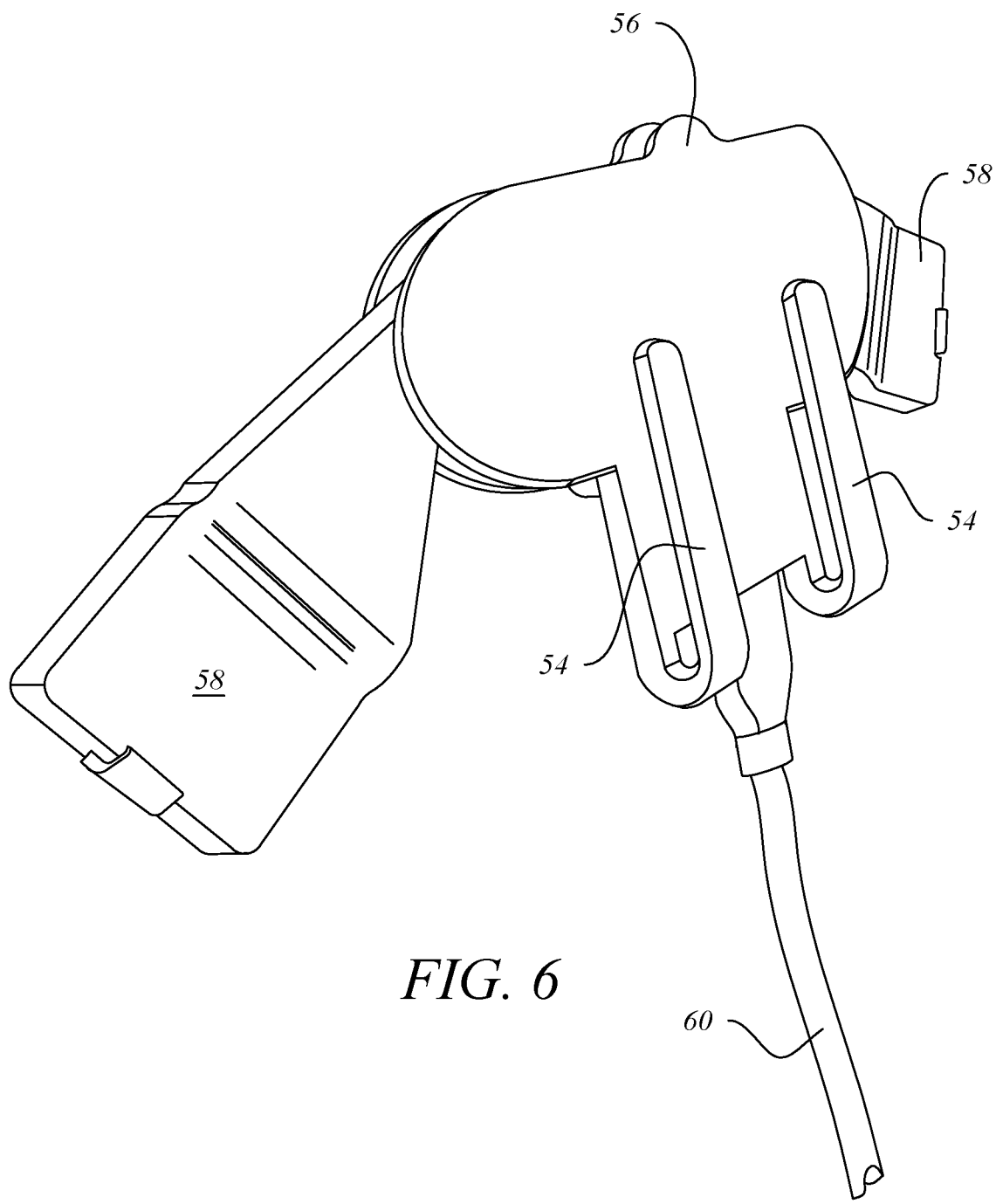
FIG. 6 is a top perspective view of the personal proximity alert device of FIGS. 4 and 5 when detached from the cap.

One embodiment of a personal proximity alert device 52 is further depicted and described in relation to FIGS. 4-6 of the drawings. Referring to FIG. 4, a conventional cap 50 with a bill and an adjustable headband is depicted with a personal proximity alert device 52 that is clipped onto the bill of cap 50 by a plurality of laterally spaced-apart, resilient plastic spring clips 54. A selectively detachable power cord 60 is also disclosed, which can be connected to an electrical AC/DC charger (not shown) for recharging a small battery disposed inside personal proximity alert device 52 between uses. Alternatively, power cord 60 can be attached to a small DC battery pack worn elsewhere on the person or apparel of a user.

Referring again to FIGS. 4-6, cap 50 is depicted in an inverted position in FIG. 5 and shows the underside of cap 50 with personal proximity alert sensor 52 clipped to the underside of the bill portion of cap 50 and power cord 60 again projecting forwardly from cap 50 as it would be if being used to recharge personal proximity alert sensor 52 between uses. Referring to FIG. 6, personal proximity alert device 52 is shown detached from cap 50 shown in FIGS. 4-5, but still has power cord 60 releasably connected to the front side of body portion 56. Wing members 58 are depicted as being pivotably attached to body portion 56 of personal proximity alert device 52. Body portion 56 and wing members 58 desirably comprise other components of behavior modification system 10 of the invention as previously discussed in relation to personal proximity alert device 13 of the invention. It should be understand by the reader that personal proximity device 52 can, in some instances and embodiments, be reduced in size sufficiently that most of the elements can be concealed inside the bill of cap 50. Sensors inside wing members 58 can be configured to alert the user to something (including without limitation the fingers or hands of the user) disposed within a monitored field such as the personal protection zone of the device, and can do so based upon various available technologies including infrared, ultrasonic, electronic, and the like, to trigger a visual, audible or tactile alert for the user.

Alert behavior modification system 10 of the invention can in some embodiments detect either passive objects disposed within or approaching the personal protection zone of a moving user of the device or moving objects approaching proximity sensors disposed within the personal protection zone of an active or passive user of proximity alert device 13, 52.

Figure 7:
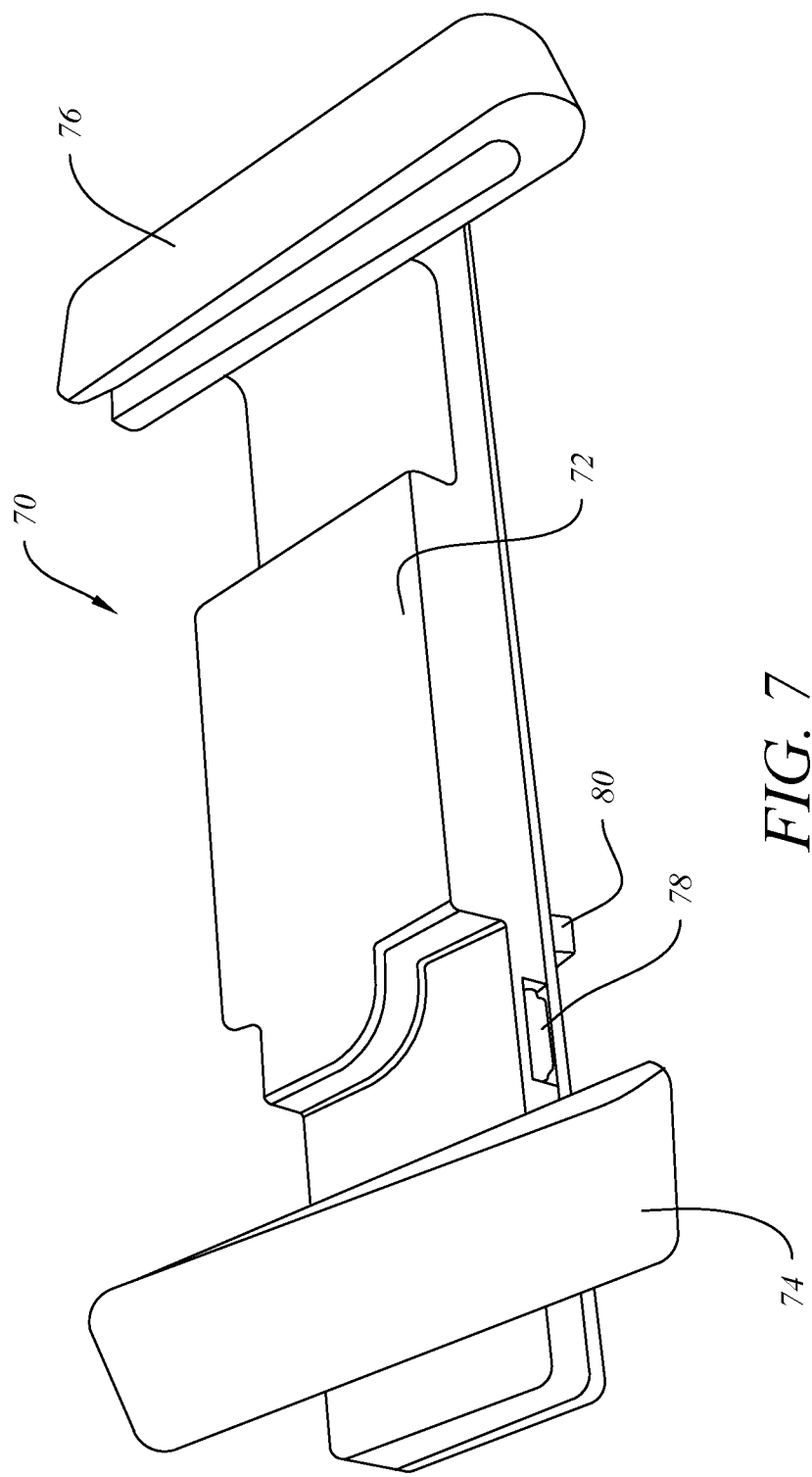
FIG. 7 is a top perspective view of another embodiment of an alert notification member of the invention.
Figure 8:
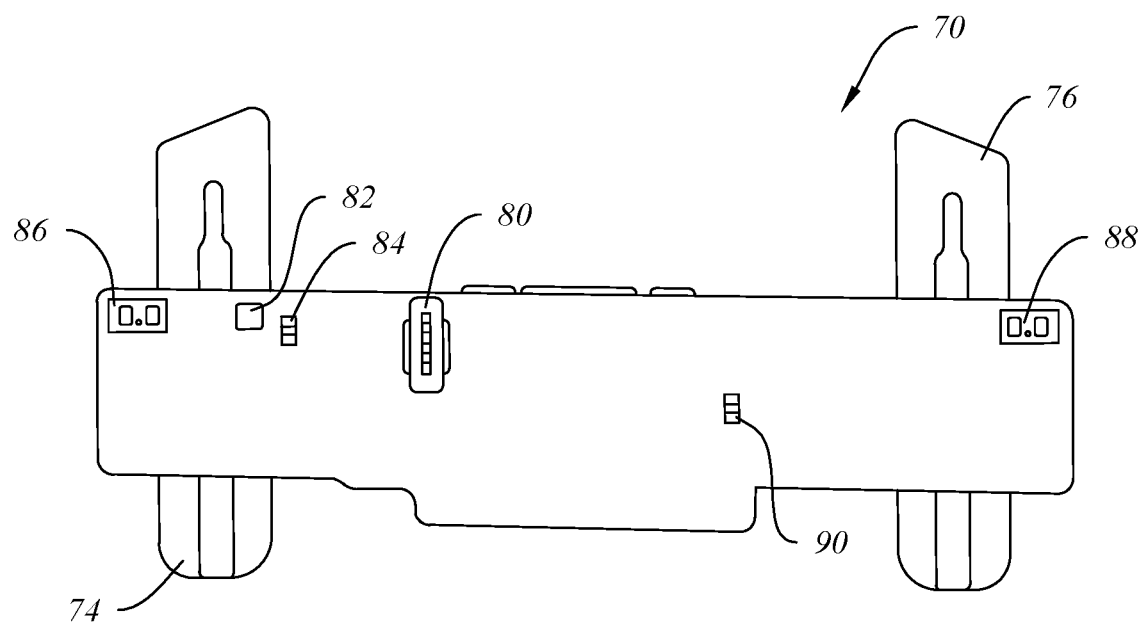
FIG. 8 is a bottom plan view of the alert notification member of FIG. 7.
Figure 9:
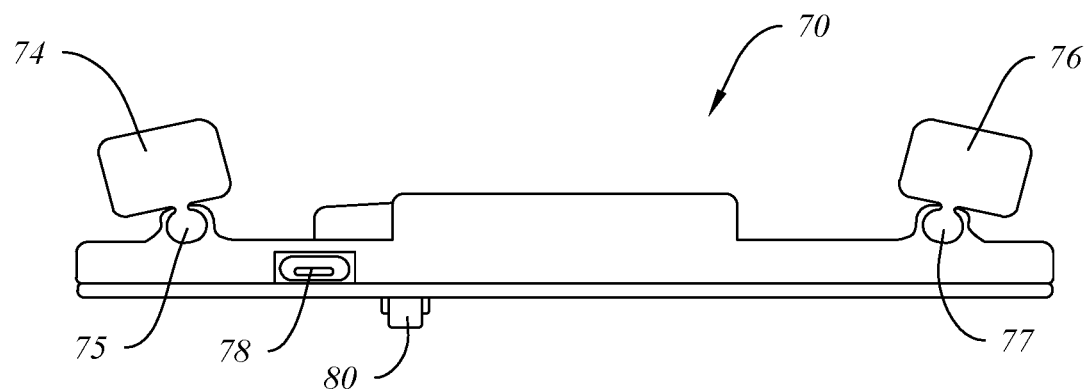
FIG. 9 is a front elevation view of the alert notification member of FIG. 7.

Referring to FIGS. 7-9, another embodiment of the invention is disclosed that comprises personal proximity alert device 70 having a body 72 with opposed, positionally adjustable engagement clips 74, 76 mounted on swivel pedestals 75, 77 that are releasably attachable to an article of clothing or other article, such as the bill of a cap, a backpack strap, belt or the like. Referring to FIGS. 8-9, device 70 further comprises USB battery charging port 78, communications port 80, power/reset button 82, battery status light 84, proximity sensors 86, 88 and unit status light 90.

Figure 10:
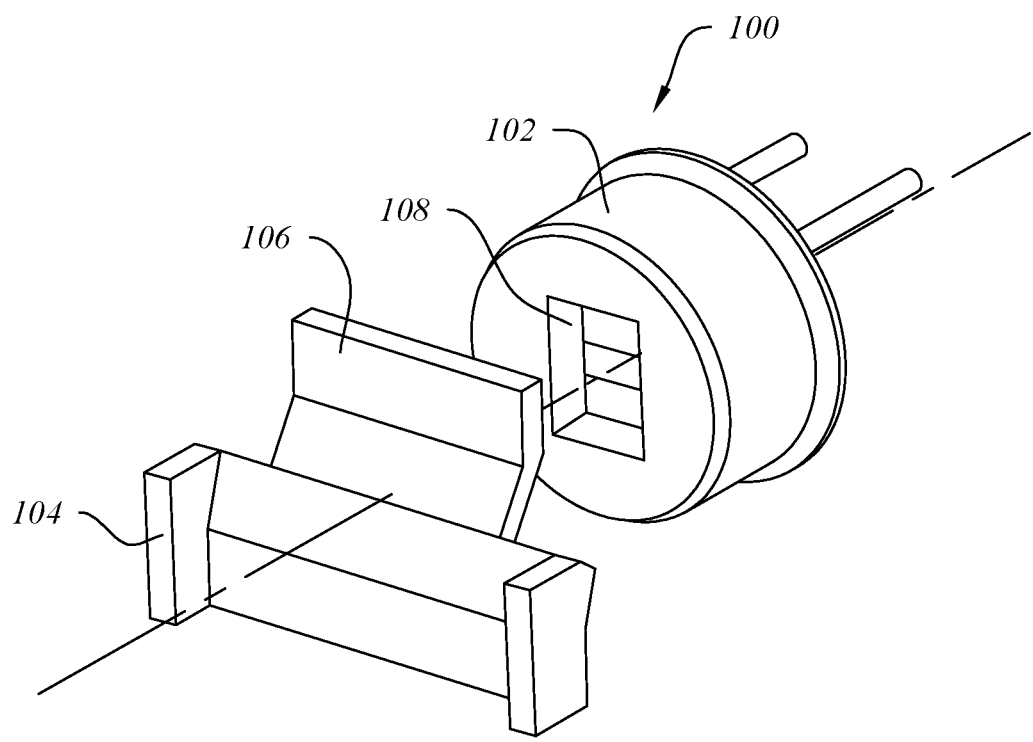
FIG. 10 is a front perspective view of an embodiment of an IR sensing apparatus for use in some preferred embodiments of the invention.
Figure 11:
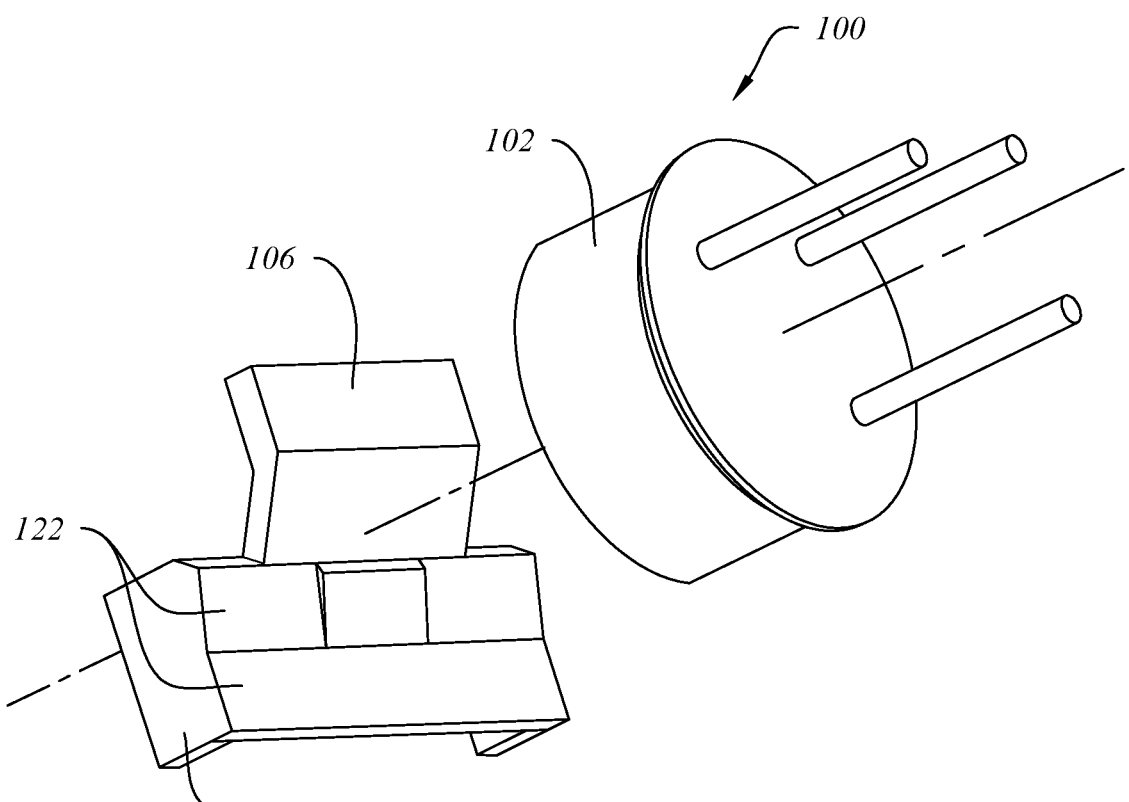
FIG. 11 is a rear perspective view of the IR sensing apparatus of FIG. 9.
Figure 12:
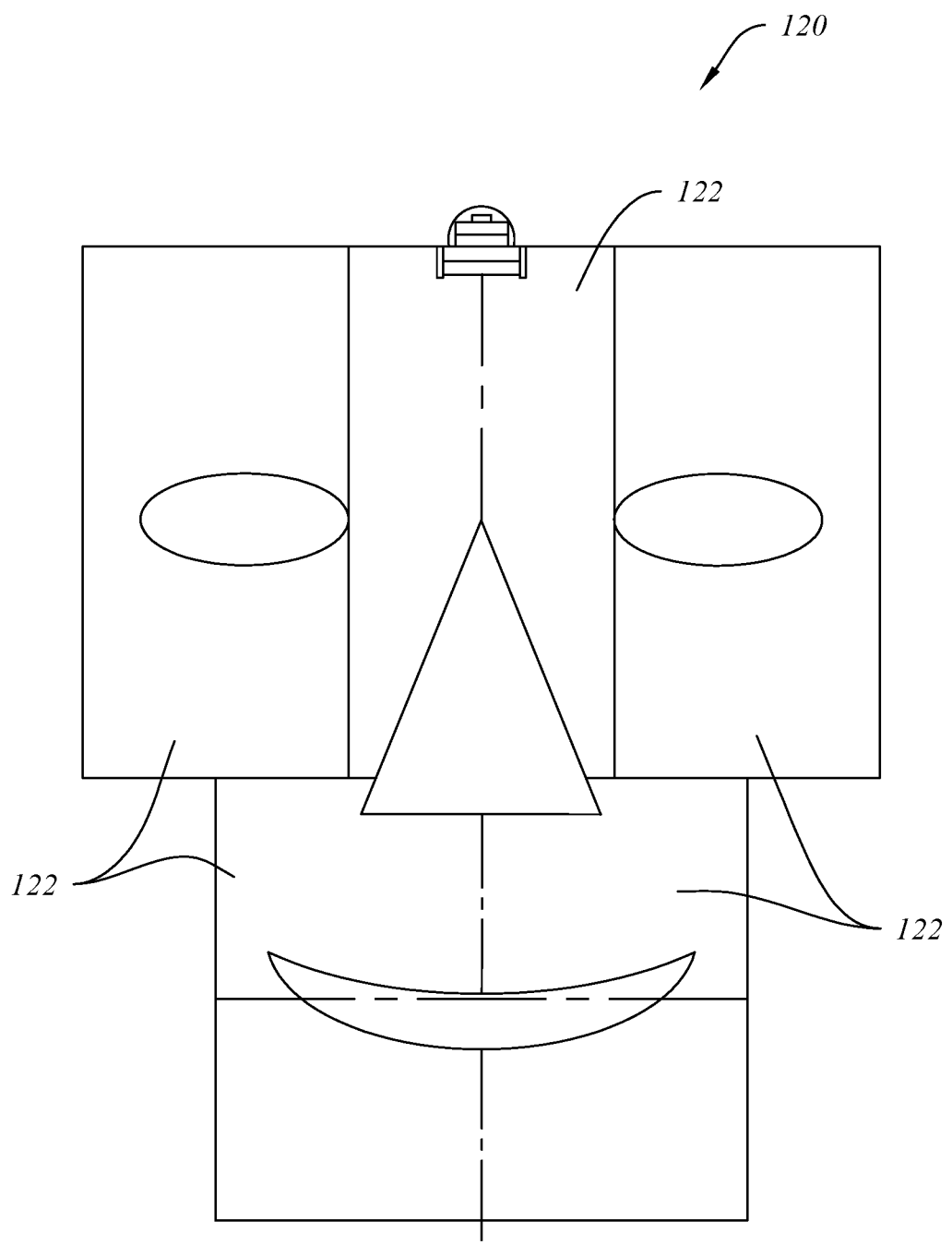
FIG. 12 is a diagrammatic view depicting an embodiment of how sections of an infrared image of the face of a user can be mapped onto an IR sensor using a mirror having differently focused facets.

Referring to FIGS. 10-12, according to one embodiment of the invention, a PIR (Passive InfraRed) Smart Hat is disclosed that is similarly configured to the devices shown and described in relation to FIGS. 4-9 except that it is specially designed to monitor the heat of a user's face and detect changes in temperature. The temperature can be monitored continuously, but to save battery life is more likely determined at periodic intervals to determine a ΔT that can be recorded or averaged to produce a digital or graphical readout. According to one preferred embodiment of the invention, because the hands and fingers are about 5 degrees colder than the face, sensor assembly 100 can detect the presence of a hand when it is in the field of view of the PIR 102. PIR sensor 102 desirably has two sensors 108 that monitor the sensed heat separately. If the difference, which range can be adjusted, is too great, it will trigger an alert. This design can be constructed using a multi-panel Fresnel mirror 104 (chrome plated plastic attachable by mount 106) to focus different portions of the face of a user on the two sensors 108 within PIR 102. One sensor receives heat from the center of the face while the other sensor receives heat from around the center, thereby generating a profile of the IR energy (using the mirrors to reflect the face image back onto the sensor). If the hand or fingers of a user (or someone else) enter the zone surrounding the center of the face, PIR 102 will detect the difference in heat signatures, and can accurately and dependably trigger an alert. FIG. 12 is a diagrammatic view 120 depicting an embodiment of how sections 122 of an infrared image of the face of a user can be mapped onto an IR sensor using a mirror having differently focused facets.

It will become apparent to those of ordinary skill in the art upon reading this specification in relation to the accompanying drawings that various other modifications and alterations to the disclosed apparatus and methods can also be made, and it is intended that the scope of the invention disclosed herein be limited only by the broadest interpretation of the appended claims to which the inventors are legally entitled.

We claim:

1. A personal proximity alert device comprising a detection member and an alert notification member that communicate cooperatively to activate an audible, visible or tactile alert to a user whenever a hand of the user is moved toward the face of the user;
   the detection member comprising an infrared sensor; and
   the alert notification member being operatively linked to a temperature recording device configured to monitor and store a facial temperature of the user at requisite times for the purpose of ascertaining whether the user may have become infected by an infectious pathogen.

2. The device of claim 1 wherein the alert to the user is triggered sufficiently in advance of any physical contact between the hand and face of the user that the user is able to control the movement of the hand of the user toward the face of the user to prevent such physical contact from occurring.

3. A behavior modification system comprising the personal proximity alert device of claim 1 in combination with a power supply and a preprogrammed or programmable processor operatively coupled to the detection member and to the alert notification member.

4. The system of claim 3 wherein the programmable processor is controllable to selectively determine the proximity between the hand and face of the user when the alert is activated.

5. The system of claim 3 wherein the programmable processor is controllable to selectively determine the maximum duration of the alert following activation.

6. The device of claim 1 wherein the detection member and the alert notification member are releasably attachable to a bill of a cap wearable by the user.

7. The device of claim 6 wherein the temperature recording device is also attachable to the bill of a cap wearable by the user.

8. The device of claim 1 wherein the detection member further embodies detection technology selected from the group consisting of magnetic, acoustic, radio frequency, motion or optical detection technology.

9. The device of claim 1 wherein the proximity alert notification member terminates an alert when both hands of the user are withdrawn beyond a predetermined proximity to the face of the user.

10. The system of claim 3 wherein the proximity alert notification member is operable without user interaction.

11. The system of claim 3 wherein the proximity alert notification member is inoperable without user interaction.

12. The system of claim 3 further comprising a touch counter.

13. A behavior modification system useful for educating, sensing, reminding, alerting, warning and conditioning users to avoid behaviors selected from the group consisting of facial self-touching and close interpersonal contacts or grouping to thereby reduce the likelihood and transmission rate of viral infections such as corona virus (COVID-19), influenza and other pathogens, the system comprising at least one personal proximity alert device further comprising at least one detector device and at least one alert notification member;

the detection member comprising an infrared sensor; and the alert notification member being operatively linked to a temperature recording device configured to monitor and store a facial temperature of the user at requisite times for the purpose of ascertaining whether the user may have become infected by an infectious pathogen.

14. The behavior modification system of claim 13 further comprising a digital controller and at least one audible visual or tactile alert generator.

15. The behavior modification system of claim 13 further comprising a power supply.

16. The behavior modification system of claim 13 further comprising a timer.

17. The behavior modification system of claim 13 further comprising a touch counter.

18. The behavior modification system of claim 13 further comprising a data storage member.

19. The behavior modification system of claim 13 further comprising a digital display.

20. The behavior modification system of claim 13 further comprising a transmitter/receiver.

* * * * *